US011613757B2

(12) United States Patent
Dukkipati et al.

(10) Patent No.: US 11,613,757 B2
(45) Date of Patent: Mar. 28, 2023

(54) PROCESS FOR EXTRACELLULAR SECRETION OF BRAZZEIN

(71) Applicant: Magellan Life Sciences Private Limited, Hyderabad (IN)

(72) Inventors: Abhiram Dukkipati, Hyderabad (IN); Aakruthi Vasihnavi Balagangadhar, Secunderabad (IN)

(73) Assignee: MAGELLAN LIFE SCIENCES LTD., London (GB)

( * ) Notice: Subject to any disclaimer, the term of this patent is extended or adjusted under 35 U.S.C. 154(b) by 191 days.

(21) Appl. No.: 16/073,702

(22) PCT Filed: Jan. 27, 2017

(86) PCT No.: PCT/IN2017/050039
§ 371 (c)(1),
(2) Date: Jul. 27, 2018

(87) PCT Pub. No.: WO2017/130222
PCT Pub. Date: Aug. 3, 2017

(65) Prior Publication Data
US 2019/0153455 A1    May 23, 2019

(30) Foreign Application Priority Data

Jan. 27, 2016   (IN) .............................. 201641002922

(51) Int. Cl.
*C12N 15/70*      (2006.01)
*C07K 14/43*      (2006.01)
*A23L 27/30*      (2016.01)

(52) U.S. Cl.
CPC .............. *C12N 15/70* (2013.01); *A23L 27/31* (2016.08); *C07K 14/43* (2013.01)

(58) Field of Classification Search
CPC .......... C12N 15/70; A23L 27/31; C07K 14/43
See application file for complete search history.

(56) References Cited

U.S. PATENT DOCUMENTS

| 6,500,613 | B1 * | 12/2002 | Briles | .................. | G11B 25/043 |
| | | | | | 435/6.15 |
| 8,592,181 | B2 | 11/2013 | Kong | | |
| 2003/0219854 | A1 * | 11/2003 | Guarna | ................ | C07K 1/1075 |
| | | | | | 435/68.1 |
| 2007/0059713 | A1 * | 3/2007 | Lee | ...................... | C12Q 1/6848 |
| | | | | | 435/6.11 |
| 2012/0220756 | A1 | 8/2012 | Kong | | |

FOREIGN PATENT DOCUMENTS

| CN | 101570754 A | 11/2009 |
| WO | 0061759 A1 | 10/2000 |
| WO | 2011025077 A1 | 3/2011 |
| WO | 2012127002 A1 | 9/2012 |

OTHER PUBLICATIONS

Berlec et al. Appl Microbiol Biotechnol, 73:158-165 (Year: 2006).*
Lee et al., Bull Korean Chem, 2010, vol. 31, No. 12, pp. 3830-3833 (Year: 2010).*
Leone et al. Acetate: friend or foe? Efficient production of a sweet protein in *Escherichia coli* BL21 using acetate as a carbon source. 2015. Microbial Cell Factories 14:106, 1-10 (Year: 2015).*
Hoffmann et al. Lactose Fed-Batch Overexpression of Recombinant Metalloproteins in *Escherichia coli* BL21 (DE3): Process Control Yielding High Levels of Metal-Incorporated, Soluble Protein. 1995, Protein Expression and Purification, 6, 646-654 (Year: 1995).*
Lee JJ et al: "Design and Efficient Soluble Expression of a Sweet Protein, Brazzein and Minor-Form Mutant" Bulletin of the Korean Chemical Society; 2010; vol. 31(12) pp. 3830-3833.
Kotzsch A et al: "A secretory system for bacterial production of high-profile protein targets" Protein Science; 2011; vol. 20(3); pp. 597-609.
Ming D et al: "Brazzein, a new high-potency thermostable sweet protein from Pentadiplandra brazzeana B." FEBS Letters 355; 1994; pp. 106-108.
Assadi-Porter FM et al: "Sweetness Determinant Sites of Brazzein, a Small, Heat-Stable, Sweet-Tasting Protein" Archives of Biochemistry and Biophysics; 2000; Volumr 376(2); pp. 259-265.
Written Opinion of the International Searching Authority for PCT/IN2017/050039 dated Mar. 31, 2017; 6 pages.
International Search Report for PCT/IN2017/050039 dated Mar. 31, 2017; 2 pages.
Supplemental European Search Report on European Patent Application No. EP17743868.6 dated Jun. 3, 2019; 8 pages.
Database Geneseq [Online]; "Pentadiplandra brazzeana mutant brazzein protein (D28A), SEQ ID 88"; XP002791411, retrieved from EBI accession No. GSP: AZF53890; Apr. 14, 2011; 1 page.
Database JPO Proteins [Online]; "JP 2002541807-A/17: Protein sweetener"; XP002791412, retrieved from EBI accession No. JPOP: BD627367; Aug. 24, 2012; 1 page.
Database Geneseq [Online]; "LQ2 signal-del-pGlu1 mature P. brazzeana brazzein fusion protein, SEQ 48"; XP002791413, retrieved from EBI accession No. GSP: BAA22216; Nov. 22, 2012; 1 page.
Ming, Ding, et al.; "Brazzein, a new high-potency thermostable sweet protein from Pentadiplandra brazzeana B." FEBS Letters 355(1); Nov. 1994; pp. 106-108.
Assadi-Porter, F.M., et al.; "Efficient production of recombinant brazzein, a small, heat-stable, sweet-tasting protein of plant origin"; Archives of Biochemistry and Biophysics 376(2); Apr. 2000; pp. 252-258.
Assadi-Porter, F.M., et al.; "Sweetness determinant sites of brazzein, a small, heat-stable, sweet-tasting protein"; Archives of Biochemistry and Biophysics 376(2); Apr. 2000; pp. 259-265.
Jin, Zheyuan, et al.; "Critical regions for the sweetness of brazzein"; FEBS Letters 544; May 2, 2003; pp. 33-37.
Hellekant, Goran, et al.; "Brazzein a Small, Sweet Protein: Discovery and Physiological Overview"; Chemical Senses 30 (suppl 1); Jan. 2005; pp. i88-i89.
Berlec, A., et al.; "Expression of the sweet-tasting plant protein brazzein in *Escherichia coli* and Lactococcus lactis: a path toward sweet lactic acid bacteria"; Applied Microbiology and Biotechnology 73(1); May 2006; pp. 158-165.
Walters, D. Eric, et al.; "Design and Evaluation of New Analogs of the Sweet Protein Brazzein"; Chemical Senses 34(8); Aug. 20, 2009; pp. 679-683.

(Continued)

Primary Examiner — Antonio Galisteo Gonzalez
Assistant Examiner — Khaleda B Hasan
(74) Attorney, Agent, or Firm — Baker & McKenzie LLP

(57) ABSTRACT

The present invention discloses a process for the secretion of brazzein in improved yield.

19 Claims, 11 Drawing Sheets

Specification includes a Sequence Listing.

(56) References Cited

OTHER PUBLICATIONS

Poirier, N., et al.; "Efficient production and characterization of the sweet-tasting brazzein secreted by the yeast *Pichia pastoris*"; Journal of Agriculture and Food Chemistry 60(39); Sep. 18, 2012; pp. 9807-9814.

Yun, Chorong, et al.; "Improved secretory production of the sweet-tasting protein, brazzein, in Kluyveromyces lactis"; Journal of Agriculture and Food Chemistry 64(32); Aug. 2016; 25 pages.

Berlec, A., et al.; "Large increase in brazzein expression achieved by changing the plasmid/strain combination of the NICE system in Lactococcus lactis"; Letters in Applied Microbiology 48(6); Mar. 30, 2009; pp. 750-755.

Assadi-Porter, Fariba, et al.; "Efficient and rapid protein expression and purification of small high disulfide containing sweet protein brazzein in *E. coli*"; Protein Expression and Purification 58(2); Dec. 3, 2007; 13 pages.

Lee, Jin-Ju, et al.; "Design and Efficient Soluble Expression of a Sweet Protein, Brazzein and Minor-Form Mutant"; Bull. Korean Chem. Soc., vol. 31, No. 12; Dec. 2010; pp. 3830-3833.

Kleiner-Grote et al., "Secretion of recombinant proteins from *E. coli*," Engineering in Life Sciences, 2018, 18, 532-550.

Elbing et al., "Growth of *E. coli* in Liquid Medium," Current Protocols in Molecular Biology, 2019. 125, e81. 2 pages. doi: 10.1002/cpmb.81.

Merriam-Webster, Definition of the Word Effective, Merriam-Webster.com, https://www.merriam-webster.com/dictionary/effective (last visited Jan. 12, 2022).

Merriam-Webster, Definition of the Word Ineffective, Merriam-Webster.com, https://www.merriam-webster.com/dictionary/ineffective (last visited Jan. 12, 2022).

* cited by examiner

PROCESS FOR EXTRACELLULAR SECRETION OF BRAZZEIN

CROSS-REFERENCE TO RELATED APPLICATIONS

This application is a U.S. National Stage Entry of International Application No. PCT/IN2017/050039 filed on Jan. 27, 2017, which claims priority to Indian Patent Application No. 201641002922 filed on Jan. 27, 2016, which are incorporated herein by reference in their entirety as set forth in full.

REFERENCE TO SEQUENCE LISTING

This application includes an electronically submitted substitute sequence listing in .txt format. The .txt file contains a sequence listing entitled "Sequence Listing-10114046-50498474-0000 ST25.txt" created on Sep. 18, 2018 and is 5248 bytes in size. The sequence listing contained in this .txt file is part of the specification and is hereby incorporated by reference herein in its entirety.

TECHNICAL FIELD OF THE INVENTION

The present invention relates to a process for the extracellular secretion of Brazzein from *E. coli* cells in enhanced yield and purity.

BACKGROUND OF THE INVENTION

Brazzein is a high-potency thermostable sweet protein, originally isolated from the fruit of the West African climbing tree *Pentadiplandra brazzeana* Baillon. (Ming and Hellekant, *FEBS Lett.* 355: 106-108, 1994). Brazzein is 2,500 times sweeter than sucrose in comparison to 2% sucrose aqueous solution and 500 times in comparison to 10% sucrose. Due to its close taste profile with sucrose compared to other protein based natural sweetners such as thaumatin or monellin, its water solubility, stability at high temperatures and at low pH, brazzein may be conveniently used in baking formulations and by industrial food manufacturers. This stability of Brazzein coupled with its sweet taste profile makes this a suitable alternative to currently available low calorie high intensity sweeteners such as sucralose, Aspartame, and *Stevia*. As a dietary protein, it is safe for consumption by diabetics. When blended with other sweeteners such as aspartame and *stevia*, Brazzein reduces their aftertaste and complements their flavour.

However, isolation of Brazzein from it natural source is expensive, and hence is not commercially feasible. Moreover, *Pentadiplandra brazzeana*, known for producing Brazzein which is found in the extracellular space of the pulp surrounding the seeds is geographically located in the West African regions of Cameroon and Gabon, isolating brazzein on a commercial scale from other regions globally becomes impractical.

In view of the many difficulties resulting from the process of extraction of Brazzein from *P. brazzeana*, several synthetic approaches have been proposed in the art to devise a mechanism for the synthesis of Brazzein.

Structurally, Brazzein comprises 54 amino acid residues, corresponding to a molecular mass of 6.5 kDa, and has been classified based on variations at the N-terminal sequences. Type I Brazzein is an unstable form composed of 54 amino acids having glutamine as the first amino acid. This unstable form may be converted to Type II Brazzein form or the Major form, wherein glutamine at the N-terminal position is converted to pyroglutamate. In Type III Brazzein or Minor form, glutamine is absent at the first amino acid position, therefore spanning an amino acid sequence of 53 amino acids. (Assadi-Porter, et al., *Arch. Biochem. Biophys.* 376: 252-258, 2000).

Other than these naturally existing forms, researchers have developed variants and multi variants of brazzein having excellent physical stability at varying temperatures, and pH ranges and possessing an excellent taste profile by mutating wild-type Brazzein through substitution of amino acids at certain positions.

A disclosure in U.S. Pat. No. 8,592,181 relates to Brazzein variants and multi variants having higher sweetness and a method for preparing the said multi-variant. A corresponding research article (Kwang-Hoon Kong et al *Bull. Korean Chem. Soc.* 2010, Vol. 31, No. 12) by the same inventor of LTS'181 has, to improve production levels of the recombinant soluble brazzein, established a new strategy using the pelB leader sequence of pectate lyase B from *Erwinia carotovora* CE for Brazzein expression. The process for Brazzein expression disclosed therein only resulted in periplasmic localization of the protein. Post fermentation, downstream processing techniques involved subjecting the induced BL21 Star (DE3) cells to centrifugation and osmotic shock. Major disadvantages of periplasmic expression and osmotic treatment to isolate the protein are its low expression yields, several centrifugation steps and a large increase in buffer volumes during the osmotic treatment, making isolation processes tedious and results in yield loss.

Fariba Assadi-Porter et al., (*Protein Expr Purif.* 2008 April; 58(2):263-8) have attempted at providing for efficient and rapid protein expression and purification of Brazzein in *E. coli*. However, the method described therein involves intracellular expression of the Brazzein protein fused to Small Ubiquitin-like Modifier protein (SUMO), followed by cleavage by SUMO protease. SUMO proteins are a family of small proteins which are covalently attached to and detached from other proteins in cells to modify their function. However, fusion of SUMO to the Brazzein protein does not modify the localization of Brazzein to the extracellular region, thereby resulting in usage of expensive and inconvenient downstream processes to isolate and purify the functional protein.

In a research article by Fariba Assadi-Porter et al., (*Arch Biochem Biophys.* 2000, 15; 376(2):252-8) Brazzein in fusion with Staphylococcal nuclease protein with single engineered cyanogen bromide cleavage site between Brazzein and Staphylococcal nuclease has been expressed. This fusion protein is expressed in insoluble inclusion bodies in *E. coli*, thus requiring extensive refolding of the followed by cleavage with cyanogen bromide to isolate functional Brazzein.

The above disclosures, relate either to periplasmic or intracellular localization of Brazzein in *E. coli*, however no attempts have been made in prior art to obtain extracellular Brazzein secretion when expressed in *E. coli* in order to increase expression yield and make downstream processing convenient and economical during industrial scale Brazzein production.

Extracellular release of proteins lodged in the periplasmic space is usually achieved by several strategies like employing leaky strains for protein expression, cell membrane permeabilization, or co-expression of release proteins. However, applications of these techniques incur exorbitant costs.

In view of the shortcomings of the methods known in the art, the present inventors have with the object of minimizing disadvantages posed by low expression yields and downstream processing of Brazzein protein, provided a convenient process for extracellular secretion of Brazzein protein from *E. coli* cells in order to increase expression yields and ease downstream processing techniques.

SUMMARY OF THE INVENTION

In a preferred aspect, the present invention provides a process for the extracellular secretion of recombinant Brazzein with improved yield comprising:
  (a) ligating a plasmid with a nucleotide sequence encoding a signal leader sequence conjugated to Brazzein to obtain a recombinant DNA construct and inserting the said construct in BL21(DE3) *E. coli* cells by transformation;
  (b) culturing the transformed cells of step (a) carrying the recombinant construct in a culture medium in the presence of Dextrose and inducing protein expression with inducing agents selected from IPTG or lactose for a period ranging from 4 hrs to 72 hrs to obtain secretion of brazzein in the culture medium, and
  (c) separating culture medium from cells after 4 to 72 hours post induction and purifying Brazzein from the clarified medium.

Accordingly, the nucleotide sequence to be ligated in the recombinant vector is such that it encodes a signal leader sequence fused to Brazzein. The signal leader sequence is selected from the group consisting of pelB, ompA, Bla, PhoA, PhoS, MalE, LivK, LivJ, MglB, AraF, AmpC, RbsB, MerP, CpdB, Lpp, LamB, OmpC, PhoE, OmpF, TolC, BtuB and LutA signal sequences.

In another aspect, the present invention provides a process for extracellular secretion of recombinant Brazzein comprising (a) inserting the pelB-Brazzein nucleotide sequence in a pET vector, wherein the said pelB-Brazzein sequence is amplified by employing primers selected from sequences represented by Seq Id No. 3, Seq Id No. 4; (b) ligating pelB-Brazzein in a pET vector to obtain a recombinant construct and inserting the said construct into BL21(DE3) *E. coli* cells by transformation; (c) culturing the transformed cells of step (b) carrying the recombinant construct in a culture medium in the presence of Dextrose and inducing protein expression with inducing agents selected from IPTG or lactose, (d) separating culture medium from cells after 4 to 72 hours post induction and purifying Brazzein from the clarified medium.

In yet another aspect, Brazzein expressed extracellularly in the culture medium is selected from the group consisting of the naturally existing wild-type functional type III Brazzein, a variant comprising a substitution at the 28$^{th}$ position of the type III brazzein from Aspartate to Alanine D28A or multi-variant of the type III.

In one aspect, the present invention provides a process for extracellular secretion of Brazzein in enhanced yield, wherein the yield of brazzein ranging between 0.5 g/l to 5 g/l. The present process is performed on a fermenter scale or at a laboratory stage in shaker flask system.

DETAILED DESCRIPTION OF DRAWINGS

Figure 3:
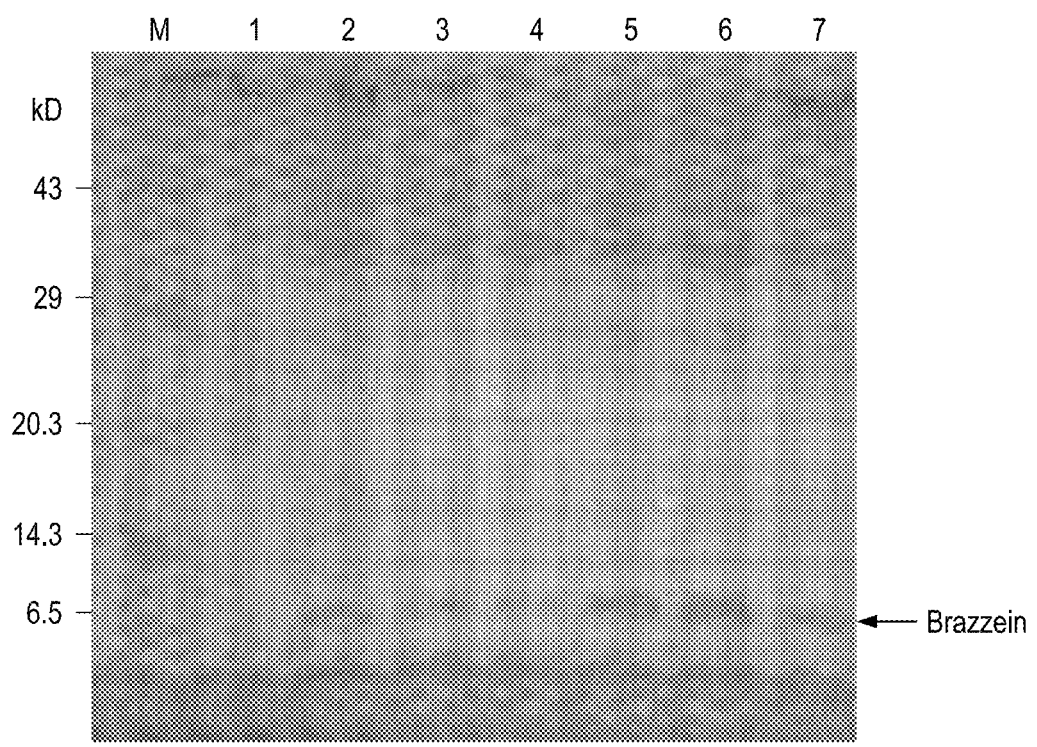

FIG. 3 depicts IPTG induced whole cell expression of Brazzein, depicted by 6.5 kiloDalton Brazzein protein. M represents Low weight molecular weight marker, Lane 1: un-induced whole cell extract, Lane 2: Whole cell extract 24 hours post-induction with 0.25 mM IPTG, Lane 3: Whole cell extract 48 hours post-induction with 0.25 mM IPTG. Lane 4: Whole cell extract 72 hours post-induction with 0.25 mM IPTG, Lane 5: Whole cell extract 24 hours post-induction with 0.50 mM IPTG, Lane 6: Whole cell extract 48 hours post-induction with 0.50 mM IPTG, Lane 7: Whole cell extract 72 hours post-induction with 0.50 mM IPTG.

Figure 4:
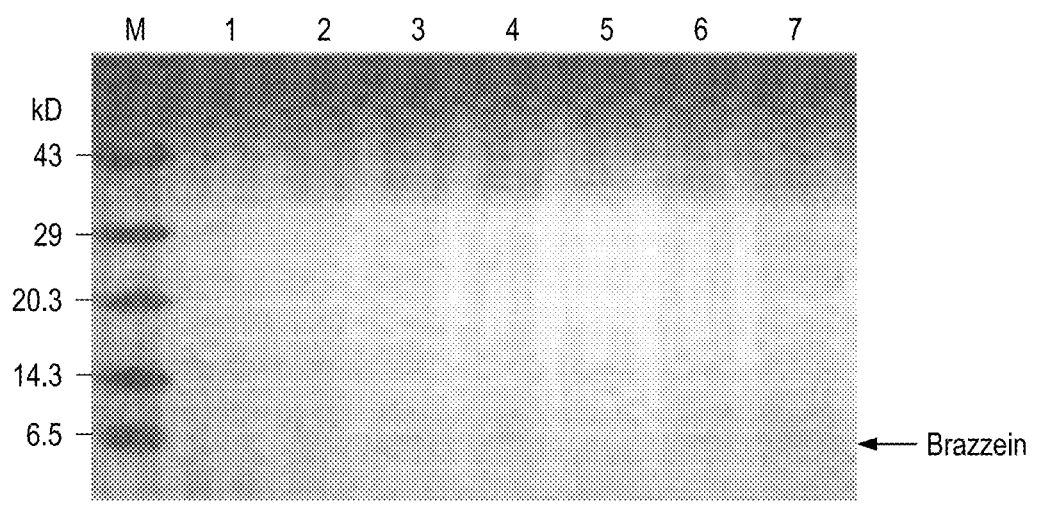
Figure 5:
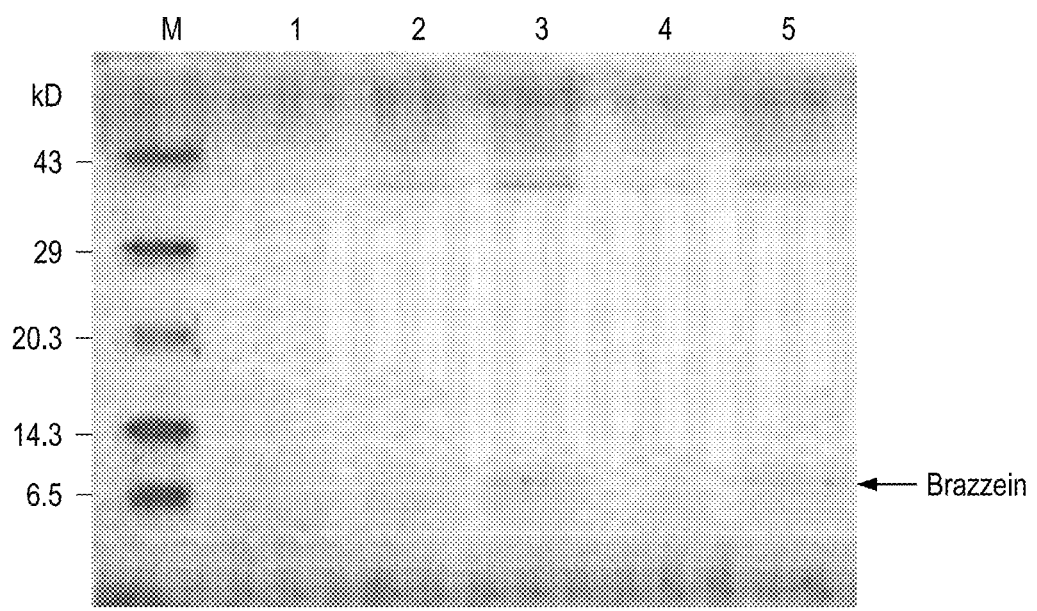
Figure 6:
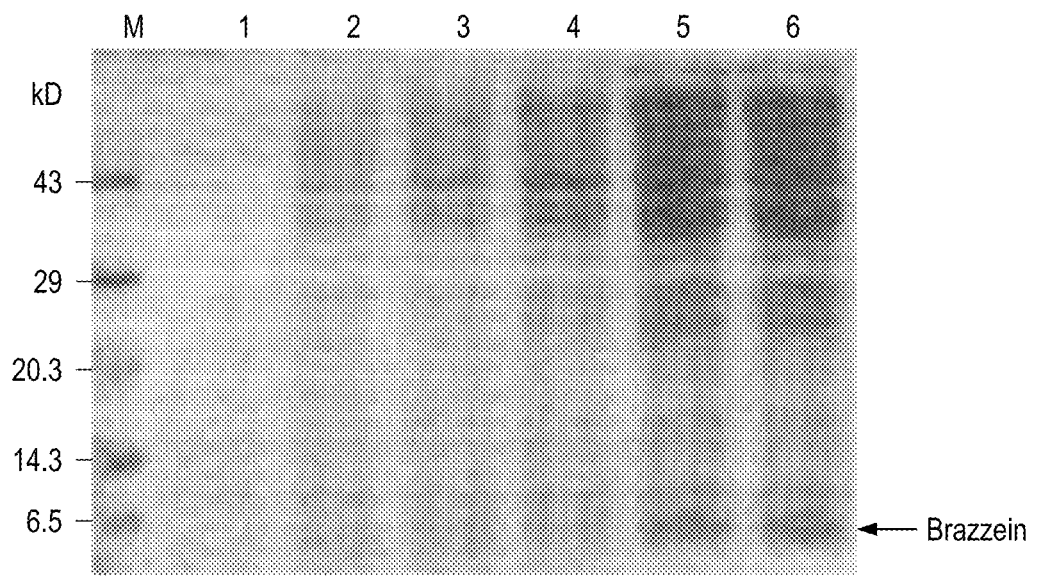
Figure 7:
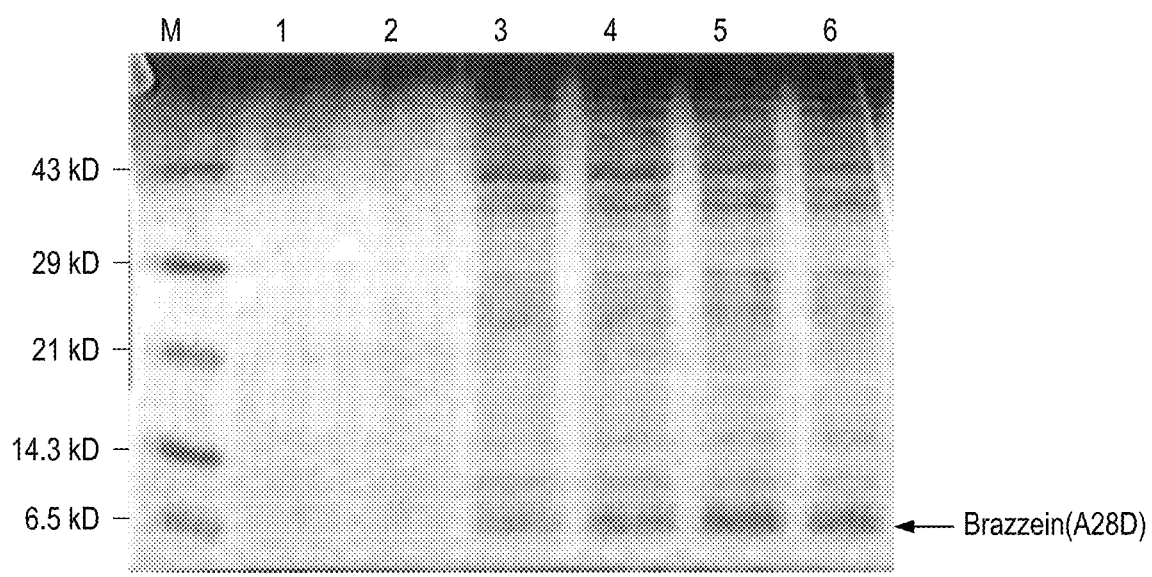

FIG. 4 depicts IPTG induced extracellular secretion of Brazzein in LB medium. M: Low weight molecular weight marker. Lane 1: Cell free supernatant of uninduced cells, Lane 2: Cell free supernatant after 24 hours induction with 0.25 mM IPTG, Lane 3: Cell free supernatant after 48 hours induction with 0.25 mM IPTG, Lane 4: Cell free supernatant after 72 hours induction with 0.25 mM IPTG, Lane 5: Cell free supernatant after 24 hours induction with 0.50 mM IPTG, Lane 6: Cell free supernatant after 48 hours induction with 0.50 mM IPTG, and Lane 7: Cell free supernatant after 72 hours induction with 0.50 mM IPTG;

FIG. 5 depicts Lactose induced extracellular secretion of Brazzein in LB medium, M represents the Low weight molecular weight marker, Lane 1: Cell free supernatant of uninduced cells, Lane 2: Cell free supernatant after 48 hours induction with 2.5 mM Lactose, Lane 3: Cell free supernatant after 72 hours of induction with 2.5 mM Lactose, Lane 4: Cell free supernatant after 48 hours induction with 5.0 mM Lactose, and Lane 5: Cell free supernatant after 72 hours induction with 5.0 mM Lactose;

FIG. 6 depicts Lactose induced extra-cellular secretion of Brazzein in TB medium, M represents the Low weight molecular weight marker, Lane 1: Cell free supernatant of uninduced cells, Lane 2: Cell free supernatant after 2 hours of induction with 5 mM Lactose, Lane 3: Cell free supernatant after 18 hours of induction with 5 mM Lactose, Lane 4: Cell free supernatant after 24 hours of induction with 5.0 mM Lactose, and Lane 5: Cell free supernatant after 36 hours of induction with 5.0 mM Lactose, Lane 6: Cell free supernatant after 48 hours of induction with 5.0 mM Lactose;

FIG. 7 depicts Lactose induced extra-cellular secretion of pelB-Brazzein(A28D) in TB media, M represents the Low weight molecular weight marker, Lane 1: Cell free supernatant of uninduced cells, Lane 2: Cell free supernatant after 4 hours of induction with 5 mM Lactose, Lane 3: Cell free supernatant after 18 hours of induction with 5 mM Lactose, Lane 4: Cell free supernatant after 24 hours of induction with 5.0 mM Lactose, and Lane 5: Cell free supernatant after 36 hours of induction with 5.0 mM Lactose, Lane 6: Cell free supernatant after 48 hours of induction with 5.0 mM Lactose. The position of mature Brazzein(A28D) is indicated by the arrow.

Figure 8:
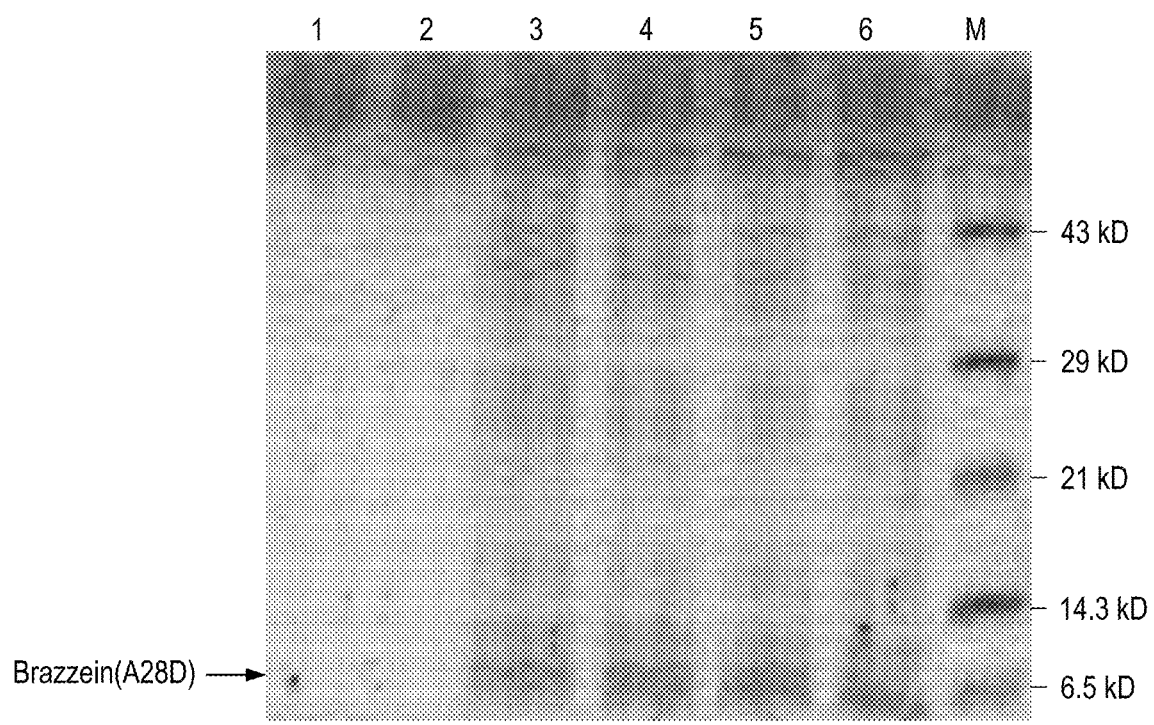

FIG. 8 depicts lactose induced extra-cellular secretion of ompA-Brazzein(A28D) in TB medium, M: Low weight molecular weight marker, Lane 1: Cell free supernatant of uninduced cells, Lane 2: Cell free supernatant after 4 hours of induction with 5 mM Lactose, Lane 3: Cell free supernatant after 18 hours of induction with 5 mM Lactose, Lane 4: Cell free supernatant after 24 hours induction with 5.0 mM Lactose, and Lane 5: Cell free supernatant after 36 hours induction with 5.0 mM Lactose, Lane 6: Cell free supernatant after 48 hours induction with 5.0 mM Lactose.

Figure 9:
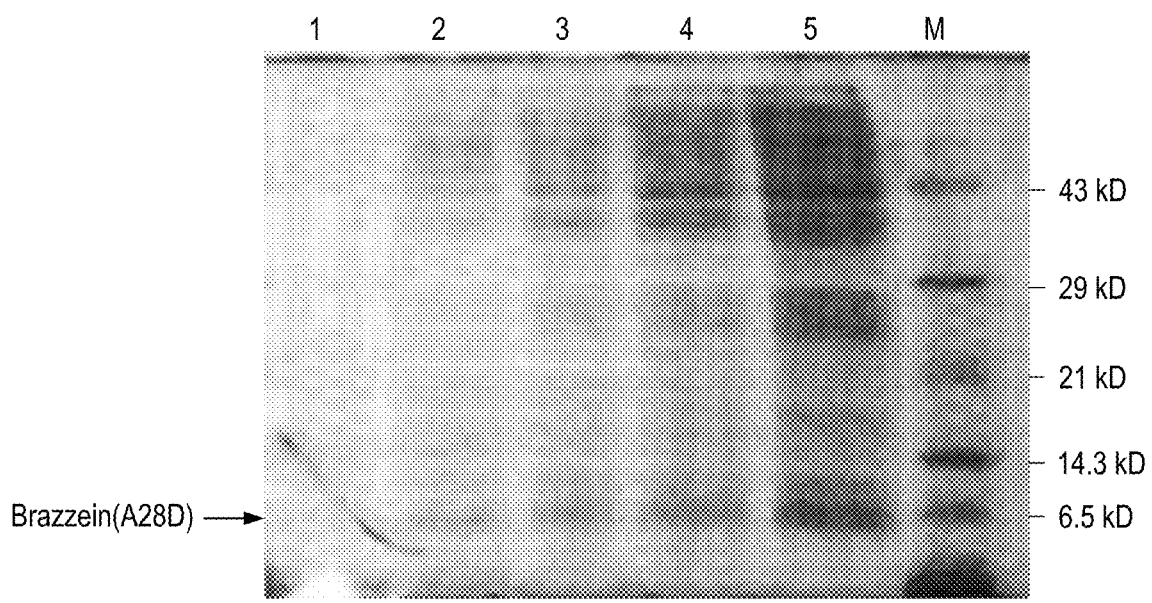

FIG. 9 depicts Lactose induced extra-cellular secretion of pelB-Brazzein(A28D) in a Fermentor, M represents the Low weight molecular weight marker, Lane 1: Cell free supernatant of uninduced cells, Lane 2: Cell free supernatant after 2 hours of induction with 5 mM Lactose, Lane 3: Cell free supernatant after 12 hours of induction with 5 mM Lactose, Lane 4: Cell free supernatant after 18 hours of induction with 5.0 mM Lactose, and Lane 5: Cell free supernatant after 24 hours of induction with 5.0 mM Lactose. The position of mature Brazzein(A28D) is indicated by the arrow.

Figure 10:
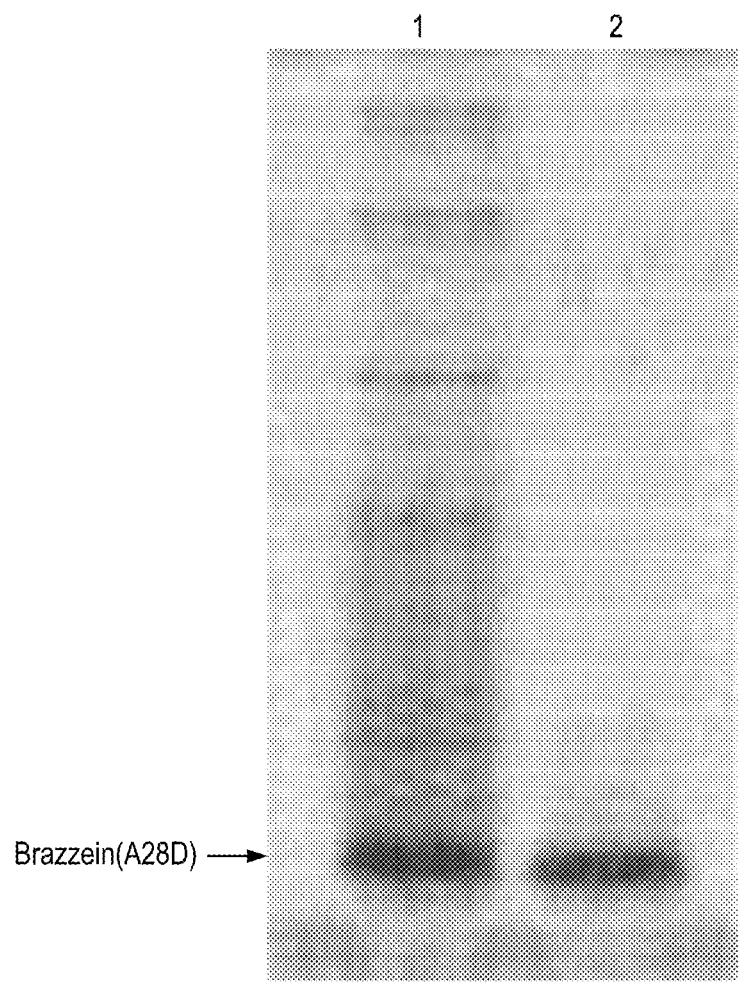

FIG. 10 depicts purification of Brazzein(A28D) from cell culture supernatant after expression in a fermentor. Lane 1: clarified sample after ammonium sulfate precipitation; Lane 2: final purified sample.

Figure 11:
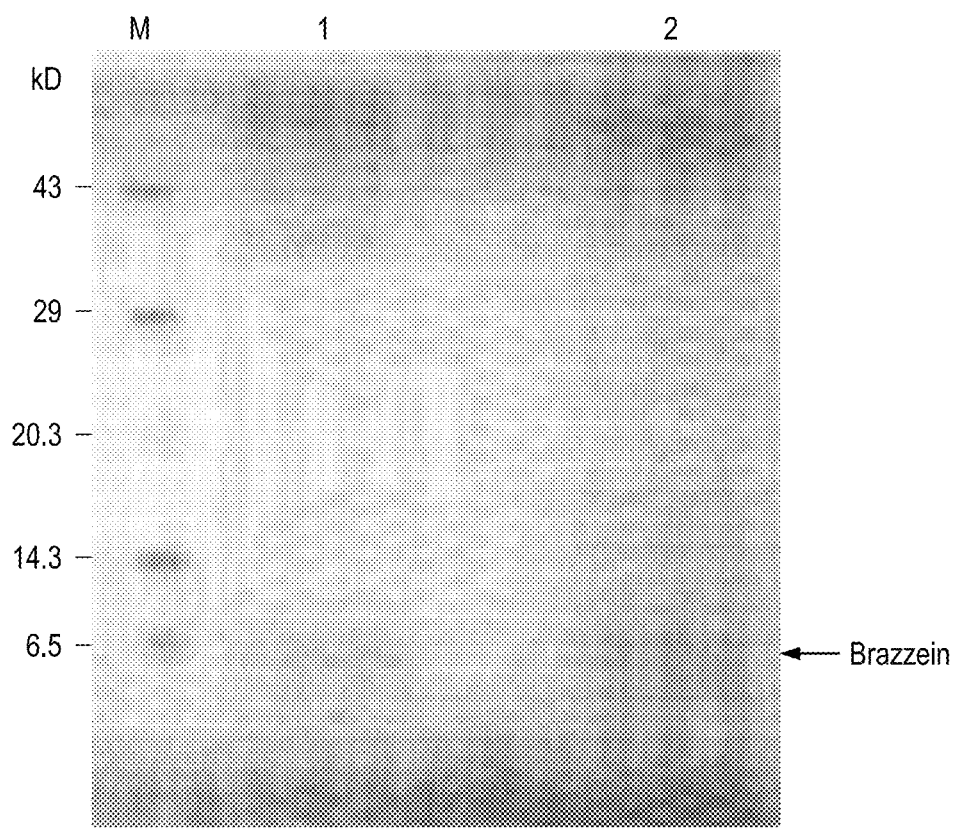

FIG. 11 depicts thermal stability of secreted brazzein synthesized by the present process, which was subjected to treatment at high temperature. M depicts the Low weight molecular weight marker. Lane 1: Untreated control sample of the cell free supernatant from a 72 hour lactose induced culture. Lane 2: Same as in Lane 1, except that the cell free supernatant was heated at 80° C. for 60 mins, centrifuged at 17,500 g and the soluble supernatant was analysed. Presence of Brazzein in lanes 1 and 2 is indicated by an arrow.

DETAILED DESCRIPTION OF THE INVENTION

The invention will now be described in detail in connection with certain preferred and optional embodiments, so that various aspects thereof may be more fully understood and appreciated.

In a preferred embodiment, the present invention provides a process for the extracellular secretion of recombinant brazzein with improved yield comprising:
  (a) ligating a nucleotide sequence encoding a signal leader sequence conjugated to Brazzein in a recombinant vector to obtain a recombinant DNA construct and inserting the said construct in BL21(DE3) E. coli cells by transformation;
  (b) culturing the transformed cells of step (a) carrying the recombinant construct in a culture medium in the presence of Dextrose and inducing protein expression with inducing agents selected from IPTG or lactose for a period ranging from 4 hrs to 72 hrs to obtain secretion of Brazzein in the culture medium, and
  (c) separating culture medium from cells and purifying Brazzein from the clarified medium Accordingly, nucleotide sequence encoding the signal leader sequence conjugated to the Brazzein is amplified with primers. The signal sequence-Brazzein amplified gene is ligated in an expression vector to obtain a recombinant vector construct which is transformed in BL21(DE3) E. coli cells. The transformed cells of E. coli carrying the recombinant construct is cultivated in a culture medium in the presence of Dextrose and inducing protein expression with inducing agents selected from IPTG or lactose for a period ranging from 4 hrs to 72 hrs, to obtain the extracellular secretion of brazzein. The cells are separated from the culture medium post induction and the culture medium also termed as the extracellular fraction is subjected to heating at temperatures as high as 90° C. to obtain Brazzein having >90% purity and in increased yield. As a result of heating, most of the endogenous E. coli proteins present in the cell free supernatant are precipitated, leaving >90% pure Brazzein in solution.

In an embodiment, the signal leader sequence to be conjugated to Brazzein is selected from the group consisting of the pelB s ompA, Bla, PhoA, PhoS, MalE, LivK, LivJ, MglB, AraF, AmpC, RbsB, MerP, CpdB, Lpp, LamB, OmpC, PhoE, OmpF, TolC, BtuB and LutA signal sequences.

In another embodiment, the present invention provides induction of signal leader-Brazzein expression in E. coli cells by addition of lactose ranging from 2.5 mM to 5 mM in the culture medium.

In yet another embodiment, the present invention provides induction of signal leader-Brazzein expression in E. coli cells by IPTG addition ranging from 0.25 mM to 0.5 mM in the culture medium.

Accordingly, extra-cellular secretion of brazzein at varying concentration of IPTG i.e. 0.25 mM and 0.5 mM at durations ranging from 24 hrs to 72 hrs is depicted in FIG. 4. Extra-cellular secretion of brazzein at varying concentration of lactose, i.e. 2.5 mM and 5 mM at durations ranging from 2 hrs to 72 hrs is depicted in FIG. 5 and FIG. 6. Post addition of the inducing agents in the culture medium, growth of cells is performed at temperatures ranging from temperatures between 25° C. to 37° C. and subjecting the cells to shaking conditions.

In another preferred embodiment, the present invention provides a process for extracellular synthesis of recombinant Brazzein with improved yield comprising:
  a) ligating a pET vector with a nucleotide sequence encoding a pelB signal leader sequence conjugated to Brazzein to obtain a recombinant DNA construct and inserting the said construct in BL21(DE3) E. coli cells by transformation;
  b) culturing the transformed cells of step (a) carrying the recombinant construct in a culture medium in the presence of Dextrose and inducing protein expression with inducing agents selected from IPTG or lactose for a period ranging from 2 hrs to 72 hrs, and
  c) separating culture medium from cells 4-72 hours post induction and purifying Brazzein from the clarified medium.

Accordingly, the process for extracellular synthesis of recombinant Brazzein conjugated to the pelB signal leader sequence comprises (a) inserting the pelB-Brazzein coding sequence in a vector, wherein the said coding sequence is amplified by employing primers selected from sequences represented by Seq Id No. 3 and Seq Id No. 4; (b) ligating pelB-Brazzein coding sequence in a pET vector to obtain a recombinant construct and inserting the said construct in BL21(DE3) E. coli cells by transformation; (c) culturing the transformed cells of step (b) carrying the recombinant construct in a culture medium in the presence of Dextrose and inducing protein expression with inducing agents selected from IPTG or lactose, (d) separating culture medium from cells post induction and purifying Brazzein from the clarified medium.

Figure 1:
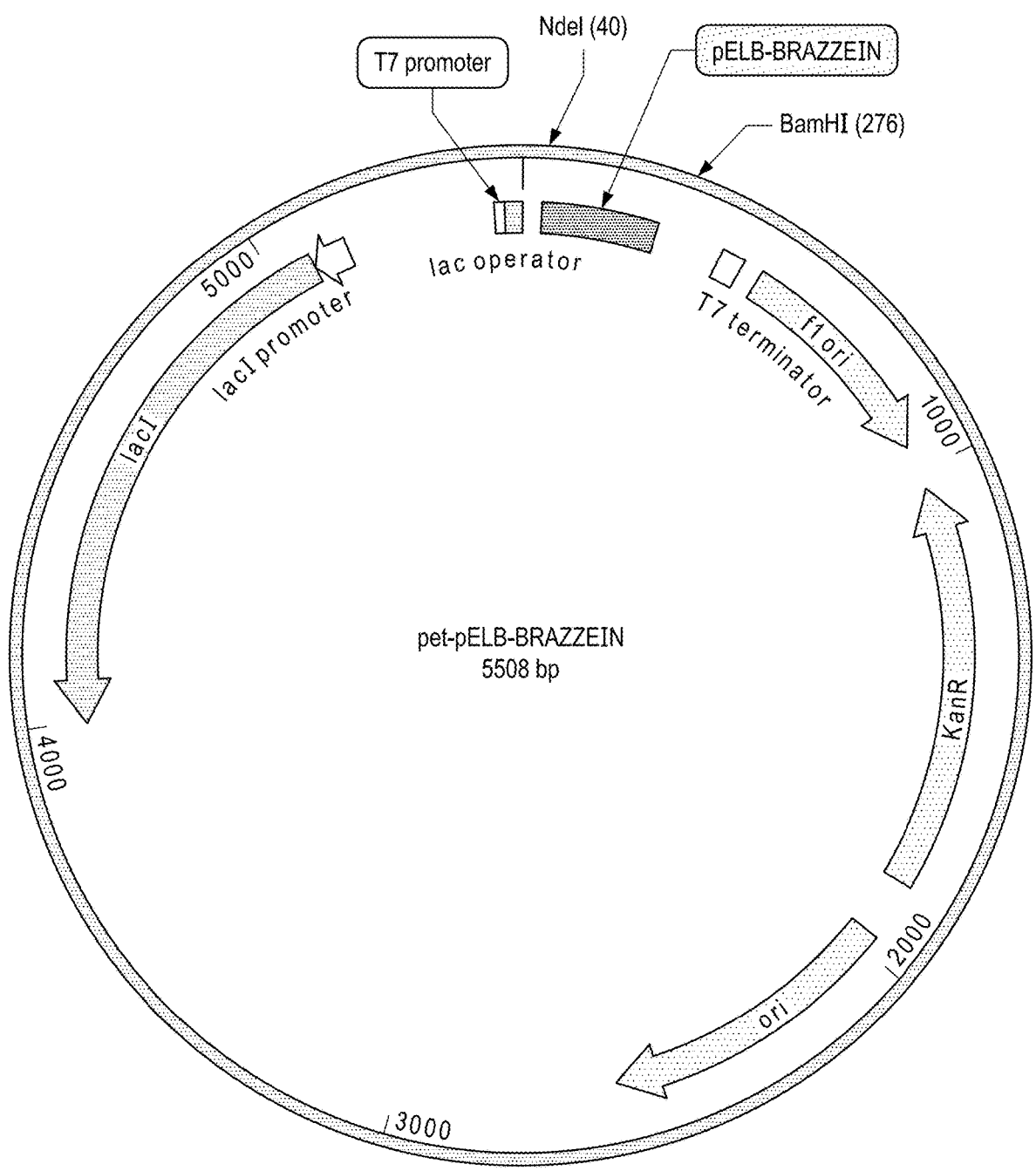
FIG. 1 depicts a vector construct comprising a lac I Promoter, LacI gene, lac operator, T7 promoter, T7 terminator and pelB-Brazzein coding nucleotide sequence.

Accordingly, the pET recombinant vector employed to carry the pelB-Brazzein nucleotide sequence is depicted in FIG. 1 of the present invention.

The molecular weight of the pelB signal leader sequence conjugated to Brazzein is 8.5 kD. However, after cleavage of the signal peptide, the molecular weight of mature Brazzein is 6.3 kD. The major band corresponding to expression of mature brazzein is indicated by arrow in FIG. 4.

In another preferred embodiment, the present invention provides a process for extracellular secretion of recombinant Brazzein with improved yield comprising:
  a) ligating a pET vector with a nucleotide sequence encoding an ompA signal leader sequence conjugated to brazzein to obtain recombinant DNA construct and inserting the said construct in BL21(DE3) E. coli cells by transformation;

b) culturing transformed cells of step (a) carrying the recombinant construct in a culture medium in presence of Dextrose and inducing protein expression with inducing agents selected from IPTG or lactose for a period ranging from 2 hrs to 72 hrs, and c) separating culture medium from cells post induction and purifying Brazzein from the clarified medium.

Accordingly, the process for extracellular synthesis of recombinant brazzein conjugated to ompA signal leader sequence comprises (a) inserting ompA Brazzein nucleotide coding sequence in a vector, wherein the said coding sequence is amplified by employing primers selected from sequences represented by Seq Id No. 4 and Seq Id No. 9; (b) ligating ompA-Brazzein coding sequence in a pET vector to obtain a recombinant construct and inserting the said construct in BL21(DE3) E. coli cells by transformation; (c) culturing the transformed cells of step (b) carrying the recombinant construct in a culture medium in presence of Dextrose and inducing protein expression with inducing agents selected from IPTG or lactose to obtain secretion of Brazzein into the culture medium, and (d) separating culture medium from cells post 4-72 hours post induction and purifying Brazzein from the clarified medium.

In yet another preferred embodiment, the present invention provides Brazzein expressed in the culture medium is selected from wild-type functional type III brazzein, a variant or multi-variant of the type III form comprising a substitution at the $28^{th}$ position of the type III brazzein from Aspartate to Alanine D28A.

Accordingly, the present invention provides the production of extracellular wild-type functional type III Brazzein represented by Seq Id No. 8, which is encoded by Seq Id No. 7. Post synthesis amino acids 1 to 22 of Seq Id No. 8 representing the pelB signal sequence are cleaved by post translational processes, to yield a mature wild-type functional type III Brazzein protein.

In one preferred embodiment, the present invention provides a process for extracellular synthesis of Brazzein in enhanced yield, wherein the yield of brazzein ranging between 0.5 g/l to 5 g/l.

Accordingly, the present process for extracellular synthesis of Brazzein is performed in a −1 or 10 litre scale fermenter.

Brazzein synthesized is found to be stable at temperatures ranging from 4° C. to 90° C.

The following examples, which include preferred embodiments, will serve to illustrate the practice of this invention, it being understood that the particulars shown are by way of example and for purpose of illustrative discussion of preferred embodiments of the invention.

EXAMPLES

Source of Expression Host:
E. coli BL21(DE3) cells were commercially obtained from BioBharati Life Sciences, Kolkata, India
Source of Expression Vector:
pET-28a vector was commercially obtained from Novagen.

Example 1: Codon Optimization and Gene Synthesis

The amino acid sequence of the Type III form of Brazzein was retrieved from Accession source P56552 (Ming D et al, FEBS Lett. 355:106-108(1994)). This amino acid sequence was back translated into a nucleotide sequence that was codon optimized for E. coli. The codon optimized gene also included an Aspartate 28 to an Alanine mutation. This variant was previously shown to exhibit a greater sweet profile in comparison to wildtype Type III Brazzein (Assadi-Porter F M, et al J L.; Arch Biochem Biophys. 2000 Apr. 15; 376(2): 259-65).

The codon optimized gene was fused at the N-terminus with a sequence encoding for the pelB leader sequence and at the C-terminus with three tandem stop codons. The final codon optimized nucleotide sequence of pelB-Brazzein is shown in SeqID 1 and the corresponding amino acid translation in SeqID 2.

pelB-Brazzein gene was synthesized by Genscript (New Jersey, USA) and cloned into pUC57 cloning vector to generate the plasmid Final PELBRAZ.

Example 2: Construction of pET-pelB-Brazzein

The PCR reaction setup is provided in the Table 1 below:

TABLE 1

| Component | Concentration |
|---|---|
| Final PELBRAZ plasmid | 50 ng |
| primer PelBLun-FNcoNde (Seq Id No. 3) | 10 picomoles |
| primer Braz-Rbam (Seq ID No. 4) | 10 picomoles |
| Pfu-X reaction Buffer | 5 μL |
| dNTP mix | 1 μM |
| Pfu-X polymerase | 0.5 μL (1 unit) |
| Sterile water | To make up the final volume to 50 μL |

TABLE 2

Stages of PCR Amplification:

| Steps | Temperature | Duration (Minutes) |
|---|---|---|
| 1 | 95° C. | 5 min |
| 2 | 95° C. | 1 min |
| 3 | 55° C. | 0.5 min |
| 4 | 72° C. | 1 min |
| 5 | Steps 2, 3 and 4 were repeated 29 times | — |
| 6 | 72° C. | 10 mins |
| 7 | 8° C. | hold |

Figure 2:
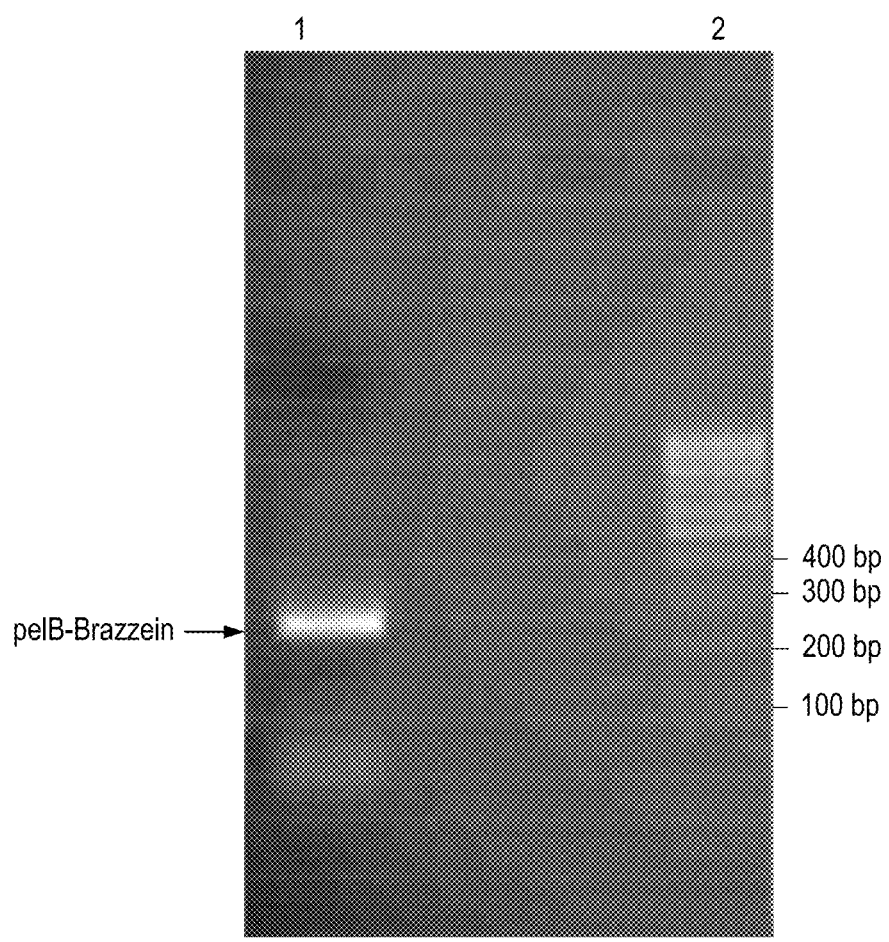
FIG. 2 depicts PCR amplification of pelB-Brazzein recombinant construct wherein Lane 1 shows amplification product corresponding to pelB-Brazzein and Lane 2 shows 100 bp DNA ladder.

The PCR amplification reaction was analyzed on a 1.6% (w/v) Agarose gel. The approximate 250 bp PCR amplification product (FIG. 2) corresponding to pelB-Brazzein was excised from the gel and purified using a commercially available kit. The purified product was digested with NdeI and BamHI for 4 hours at 37° C. and purified using a PCR spin column kit. This was ligated with pET-28a vector that was previously digested with NdeI and BamHI and gel purified. The ligation mixture was transformed into DH5 alpha competent cells. The transformed cells were plated out on LB plates containing 50 μg/mL Kanamycin and incubated overnight at 37° C. Single colonies were picked from the plate into 5 mL LB broth containing 50 ug/mL Kanamycin and grown for 16 hrs in an orbital shaker at 37° C. and 210 rpm. Plasmid DNA was isolated from the cultures and analysed by DNA sequencing. A plasmid clone containing the desired pelB-Brazzein insert was identified and labelled as pET-pelB-Brazzein and used for protein expression studies.

Example 3: Construction of pET-pelB-Brazzein (A28D)

In order to create wild-type TypeIII Brazzein, amino acid residue number 50 of pelB-Brazzein was mutated from an Alanine to an Aspartate and is referred to as pelB-Brazzein (A28D).

The first PCR reaction was setup with final PELBRAZ plasmid, primer PelBLun-FNcoNde (Seq Id No. 3), primer BRAZ-A28DRSOE (Seq Id No. 5), Pfu-X reaction buffer, dNTP mix, Pfu-X polymerase and sterile water was used to make up the final PCR reaction solution volume to 50 μL. The specific concentrations of the said components are provided in Table 3.

Seq Id No. 3:
5'-GCGCGCCCATGGCATATGAAATACCTGCTGCCGACCGC-3'

Seq Id No. 5:
5'-CACCGCTACGCGCATGTTTATCCAGTTTACAGTCGTAGTTACATTGGTTCGC-3'

TABLE 3

PCR solution for the first reaction

| Components | Concentration |
| --- | --- |
| Final PELBRAZ plasmid | 50 ng |
| PelBLun-FNcoNde (Seq Id No. 3) | 10 picomoles |
| BRAZ-A28DRSOE (Seq Id No. 5) | 10 picomoles |
| Pfu-X reaction Buffer | 5 μL |
| dNTP mix | 1 μM |
| Pfu-X polymerase | 0.5 μL (1 unit) |
| Sterile water | To make up the final volume to 50 μL |

TABLE 4

Reaction Conditions
Stages of PCR Amplification:

| Steps | Temperature | Duration (Minutes) |
| --- | --- | --- |
| 1 | 95° C. | 5 min |
| 2 | 95° C. | 1 min |
| 3 | 55° C. | 0.5 min |
| 4 | 72° C. | 1 min |
| 5 | Steps 2, 3 and 4 were repeated 29 times | — |
| 6 | 72° C. | 10 mins |
| 7 | 8° C. | hold |

PCR amplification reaction was analyzed on a 1.6% (w/v) Agarose gel. The approx. 170 bp PCR amplification product was excised from the gel and purified using a commercially available gel extraction kit. This purified fragment was labelled as Frag 1.

The second PCR reaction was setup with: Final PELBRAZ plasmid, primer BRAZ-A28DFSOE (Seq Id No. 6), primer Braz-Rbam (Seq Id No. 4), Pfu-X reaction buffer, dNTP mix, Pfu-X polymerase and sterile water was used to make up the final volume of the second reaction solution to 50 uL.

Seq Id No. 6:
5'-GATAAACATGCGCGTAGCGGTG-3'

Seq Id No. 4:
5'-GCGCGCGGATCCTCATTATTAATATTCACAGTAGTCACAGATACATTGCAG-3'

TABLE 5

PCR solution for the second reaction

| Components | Concentration |
| --- | --- |
| Final PELBRAZ plasmid | 50 ng |
| BRAZ-A28DFSOE (Seq Id No. 6), | 10 picomoles |
| Braz-Rbam (Seq Id No. 4), | 10 picomoles |
| Pfu-X reaction Buffer | 5 μL |
| dNTP mix | 1 μM |
| Pfu-X polymerase | 0.5 μL (1 unit) |
| Sterile water | To make up the final volume to 50 μL |

PCR amplification was performed by employing the reaction conditions and PCR parameters specified in Table 4. The PCR amplification reaction was analyzed on a 1.6% (w/v) agarose gel. The eighty base pair PCR amplification product was excised from the agarose gel and purified using a commercially available gel extraction kit. The final purified fragment was labelled as Frag 2.

The third PCR reaction comprised splicing by overlap extension PCR reaction, the said reaction setup comprising Frag1, Frag2, primer PelBLun-FNcoNde (Seq Id No. 3), primer Braz-Rbam (Seq Id No. 4), Pfu-X reaction Buffer, dNTP mix, Pfu-X polymerase and sterile water was used to make up the final volume to 50 μL.

TABLE 6

PCR solution for the third reaction

| Component | Concentration |
| --- | --- |
| Frag1 | 5 μL |
| Frag2 | 5 μL |
| primer PelBLun-FNcoNde (Seq Id No. 3) | 10 picomoles |
| primer Braz-Rbam (Seq ID No. 4) | 10 picomoles |
| Pfu-X reaction Buffer | 5 μL |
| dNTP mix | 1 μM |
| Pfu-X polymerase | 0.5 μL (1 unit) |
| Sterile water | To make up the final volume to 50 μL |

PCR amplification was performed by employing the reaction conditions and PCR parameters specified in Table 4.

The PCR amplification reaction was analyzed on a 1.6% (w/v) Agarose gel. The approximate 250 bp PCR amplification product corresponding to pelB-Brazzein(A28D) was excised from the gel and purified using a commercially available kit. The purified product was digested with NdeI and BamHI for 4 hours at 37° C. and purified using a PCR spin column kit. This was ligated with pET-28a vector that was previously digested with NdeI and BamHI and gel purified. The ligation mixture was transformed into DH5 alpha competent cells. The transformed cells were plated out on LB plates containing 50 μg/mL Kanamycin and incubated overnight at 37° C. Single colonies were picked from the plate into 5 mL LB broth containing 50 μg/mL Kanamycin and grown for 16 hrs in an orbital shaker at 37° C. and 210 rpm. Plasmid DNA was isolated from the cultures and analysed by DNA sequencing. A plasmid clone containing the desired pelB-Brazzein(A28D) insert was identified and labelled as pET-pelB-Brazzein(A28D) and used for protein expression studies.

The final nucleotide sequence of pelB-Brazzein(A28D) is shown in Seq Id No. 7 and the corresponding amino acid translation in Seq Id No. 8.

Example 4: Construction of pET-ompA-Brazzein(A28D)

The ompA-Brazzein(A28D) nucleotide sequence was PCR amplified using following primers: The PCR reaction was setup with pET-pelB-Brazzein(A28D) plasmid, primer ompANde, primer Braz-Rbam, Pfu-X reaction buffer, dNTP mix, Pfu-X polymerase and sterile water was used to make up the final volume to 50 μL. ompANde (Seq Id No. 9):

5'GCGCGCCCATGGCAATGAAAAAAACGGCAATTGCGATAGCGGTTGC
GCTAGCTGGTTTTGCCACGGTGGCGCAGGCTGACAAATGTAAAAAGG-
3'

Braz-Rbam (Seq Id No. 4):

5'GCGCGCGGATCCTCATTATTAATATTCACAGTAGTCACAGATACAT
TGCAG-3'

The PCR reaction was setup with pET-pelB-Brazzein (A28D) plasmid, primer ompANde, primer Braz-Rbam, Pfu-X reaction buffer, dNTP mix, Pfu-X polymerase and sterile water was used to make up the final volume to 50 μL.

TABLE 5

| PCR solution | |
|---|---|
| Component | Concentration |
| pET-pelB-Brazzein(A28D) plasmid | 50 ng |
| ompANde (Seq Id No. 9) | 10 picomoles |
| Braz-Rbam (Seq Id No. 4) | 10 picomoles |
| Pfu-X reaction Buffer | 5 μL |
| dNTP mix | 1 μM |
| Pfu-X polymerase | 0.5 μL (1 unit) |
| Sterile water | To make up the final volume to 50 μL |

PCR amplification was performed by employing the reaction conditions and PCR parameters specified in Table 2.

PCR amplification reaction was analyzed on a 1.6% (w/v) agarose gel. The approx. 250 bp PCR amplification product corresponding to ompA-Brazzein(A28D) was excised from the gel and purified using a commercially available gel extraction kit. The purified product was digested with NdeI and BamHI for 4 hours at 37° C. and purified using a PCR spin column kit. This was ligated with pET-28a vector that was previously digested with NdeI and BamHI and gel purified. The ligation mixture was transformed into DH5alpha competent cells. The transformed cells were plated out on LB plates containing 50 μg/mL Kanamycin and incubated overnight at 37° C. Single colonies were picked from the plate into 5 mL LB containing 50 ug/mL Kanamycin and grown for 16 hrs in an orbital shaker at 37° C. and 210 rpm. Plasmid DNA was isolated from the cultures and submitted for DNA sequencing. A plasmid clone containing the desired ompA-BRAZ insert was identified and labeled as pET-ompA-Brazzein(A28D) and used for protein expression studies.

The final nucleotide sequence of ompA-Brazzein is shown in Seq Id No. 10 and the corresponding protein expressed in Seq Id No. 11.

Example 5: Protein Expression (i) Expression of pelB-Brazzein with IPTG in LB Medium The pET-pelB-Brazzein plasmid was transformed into BL21(DE3) cells. The transformed cells were plated out on LB Agar plates containing 50 μg/mL Kanamycin and incubated at 30° C. overnight. A single colony was picked from the plate in 5 mL LB containing 50 μg/mL Kanamycin and 1% (w/v) Dextrose and grown for 16 hours at 30° C. and 180 rpm. The culture was diluted into two 250 mL baffled flasks containing 25 mL of LB supplemented with 50 μg/mL kanamycin, 0.1% dextrose and growth was continued at 30° C. and 210 rpm. When optical density (OD600) of the cultures reached 0.4, protein expression was induced by adding IPTG to a final concentration of 0.25 mM and 0.5 mM and growth continued 30° C. and 210 rpm. Samples were harvested at 24, 48 and 72 hrs post-induction by spinning down 100 μL of culture and carefully separating the supernatant from the cell pellet. The cell pellets were stored at −20° C. and the supernatants at 4° C. till further analysis by SDS-PAGE (see FIGS. 3 and 4).

(ii) Expression of pelB-Brazzein with Lactose in LB medium:

pET-pelB-Brazzein plasmid was transformed into BL21 (DE3) cells. The transformed cells were plated out on LB Agar plates containing 50 μg/mL Kanamycin and incubated at 30° C. overnight. A single colony was picked from the plate in 5 mL LB containing 50 μg/mL kanamycin and 1% (w/v) Dextrose and grown for 16 hours at 30° C. and 180 rpm. The culture was diluted into two 250 mL baffled flasks containing 25 mL of LB supplemented with 50 ug/mL kanamycin and growth was continued at 30° C. and 210 rpm. When optical density (OD600) of the cultures reached 0.4, protein expression was induced by adding Lactose to a final concentration of 2.5 mM and 5 mM and growth was continued 30° C. and 210 rpm. Samples were harvested at 24, 48 and 72 hrs post-induction by spinning down 100 μL of culture and carefully separating the supernatant from the cell pellet. The cell pellets were stored at −20° C. and the supernatants at 4° C. till further analysis by SDS-PAGE (see FIG. 5).

(iii) Expression of pelB-Brazzein with Lactose in TB Medium:

pET-pelB-Brazzein plasmid was transformed into BL21 (DE3) cells. The transformed cells were plated out on LB Agar plates containing 50 μg/mL Kanamycin and incubated at 30° C. overnight. A single colony was picked from the plate in 5 mL LB containing 50 ug/mL kanamycin and 1% (w/v) Dextrose and grown for 16 hours at 30° C. and 180 rpm. The culture was diluted into a baffled flask containing 25 mL of TB supplemented with 50 μg/mL kanamycin, 0.1% (w/v) Dextrose and growth was continued at 30° C. and 210 rpm. When optical density (OD600) of the cultures reached 9.0, protein expression was induced by adding Lactose to a final concentration of 5 mM and growth continued at 30° C. and 210 rpm. Samples were harvested at 4, 18, 24, 48 and 72 hrs post-induction by spinning down 100 μL of culture and carefully separating the supernatant from the cell pellet. The cell pellets were stored at −20° C. and the supernatants at 4° C. till further analysis by SDS-PAGE (see FIG. 6).

(iv) Expression of pelB-Brazzein(A28D) with Lactose in TB Medium:

pET-pelB-Brazzein(A28D) plasmid was transformed into BL21(DE3) cells. The transformed cells were plated out on LB Agar plates containing 50 μg/mL Kanamycin and incubated at 30° C. overnight. A single colony was picked from the plate in 5 mL LB containing 50 ug/mL kanamycin and 1% (w/v) Dextrose and grown for 16 hours at 30° C. and 180 rpm. The culture was diluted into a baffled flask containing 25 mL of TB supplemented with 50 μg/mL kanamycin, 0.1% (w/v) Dextrose and growth was continued at 30° C. and 210 rpm. When optical density (OD600) of the cultures reached 9.0, protein expression was induced by adding Lactose to a final concentration of 5 mM and growth continued 30° C. and 210 rpm. Samples were harvested at 4, 18, 24, 48 and 72 hrs post-induction by spinning down 100 μL of culture and carefully separating the supernatant from the cell pellet. The cell pellets were stored at −20° C. and the supernatants at 4° C. till further analysis by SDS-PAGE (see FIG. 7).

(v) Expression of ompA-Brazzein(A28D) with Lactose in TB Medium:

pET-ompA-Brazzein(A28D) plasmid was transformed into BL21(DE3) cells. The transformed cells were plated out on LB Agar plates containing 50 μg/mL Kanamycin and incubated at 30° C. overnight. A single colony was picked from the plate in 5 mL LB containing 50 μg/mL kanamycin and 1% (w/v) Dextrose and grown for 16 hours at 30° C. and 180 rpm. The culture was diluted into a baffled flask containing 25 mL of TB supplemented with 50 μg/mL kanamycin, 0.1% (w/v) Dextrose and growth was continued at 30° C. and 210 rpm. When optical density (OD600) of the cultures reached 9.0, protein expression was induced by adding Lactose to a final concentration of 5 mM and growth continued 30° C. and 210 rpm. Samples were harvested at 4, 18, 24, 48 and 72 hrs post-induction by spinning down 100 μL of culture and carefully separating the supernatant from the cell pellet. The cell pellets were stored at −20° C. and the supernatants at 4° C. till further analysis by SDS-PAGE (see FIG. 8).

(vi) Expression of pelB-Brazzein(A28D) in Fermentor by Fed-Batch Cultivation

Fermentor based expression of pelB-Brazzein(A28D) was carried out in a 5 l fermentor by fed-batch cultivation. pET-pelB-Brazzein(A28D) plasmid was transformed in *E. coli* BL21(DE3) cells. The transformed cells were plated out on LB Agar plates containing 50 μg/mL Kanamycin and incubated at 30° C. overnight. A single colony was picked from the plate in 5 mL LB containing 50 μg/mL kanamycin and 1% (w/v) Dextrose and grown for 16 hours at 30° C. and 180 rpm. A 1.5 mL aliquot of the overnight culture was diluted into a baffled flask containing 150 mL of LB supplemented with 50 μg/mL kanamycin, 1% (w/v) Dextrose and growth was continued for 12 hours at 30° C. and 210 rpm. 4.2 L of sterile TB medium in the fermentor were inoculated with 100 ml of this culture and supplemented with 0.1% (w/v) Dextrose and 50 μg/mL Kanamycin. During the fermentation, the temperature and pH were maintained at 30° C. and 7.0, respectively. The dissolved oxygen level was maintained at 30-40% by using air or pure oxygen and the speed was maintained at 600 rpm. After the optical density (OD600) reached 10, a final concentration of 5 mM Lactose was added to induce the expression of pelB-Brazzein (A28D). Samples of the culture were harvested at 4, 12, 18 and 24 hours post induction by spinning down 5 mL of culture and carefully separating the supernatant from the cell pellet. The cell pellets were stored at −20° C. and the supernatants at 4° C. till further analysis by SDS-PAGE (see FIG. 9).

(vii) Purification of Brazzein(A28D)

The culture from the fermentor was spun at 5000 g and the clarified cell free supernatant was transferred to a fresh container. To this, powdered 1.2 kg ammonium sulfate was slowly added with gentle stirring. The mixture was incubated for 1 hour with gentle stirring at room temperature and subsequently spun at 5000 g for 30 mins. The supernatant obtained after the spin was discarded and pellet containing precipitated brazzein and other proteins was dissolved in 200 mL of deionized water. This solution was heated to 90° C. for 1 hour and subsequently spun at 5000 g for 30 mins. The supernatant was carefully decanted and transferred to a fresh vessel and it was found that Brazzein (A28D) constitutes a major fraction of the total protein in this supernatant. The supernatant was passed through a 10 kDa MW cut-off centrifugal concentrator at 3000 g. Majority Brazzein passes through the filter membrane and is collected in the flow-through fraction while remaining higher molecular weight proteins do not pass through the membrane and are retained as the retentate fraction in the concentrator. The flow-through fraction was transferred to a 2 kDa MW cut-off centrifugal concentrator and buffer exchanged to water by repeated concentration and dilution with deionized water. This was continued till the colour of the retentate fraction in the concentrator was colourless and the flow-through fraction did not have any salty taste. During this, it was found that Brazzein was completely retained by the membrane in the retentate fraction while low molecular weight molecules passed through into the flow-through fraction (see FIG. 10).

The retentate fraction containing Brazzein was harvested into a fresh vessel and stored at 4° C. for further analysis. Protein Quantitation of the sample gave a final yield of 4.4 grams of Brazzein per litre of culture. Purity of Brazzein in lane 2 of FIG. 10 is greater than 95% pure by SDS-PAGE analysis.

(viii) Sensory Analysis of Brazzein

A portion of the purified Brazzein(A28D) was lyophilized and re-dissolved in deionized water to 1.0 mg/mL. From this, Brazzein(A28D) solutions with following concentrations were made: 0.5, 1.0, 2.0, 3.0, 4.0, 5.0, 6.0, 7.0, 8.0, 9.0, and 10.0 μg/mL. A 1% (w/v) sucrose solution, the lowest concentration of sucrose detectable by humans, was used as a reference. The taste panel consisted of fifteen females and fifteen males with normal health and normal sense of taste. Two-hundred-microliter samples were applied to the anterior region of the tongue. After each test, the mouth was rinsed with tap water. The tasters sampled from the lower concentration samples to higher. Each taster chose the first sample that could be sensed for sweetness. Sweetness potencies were reported relative to sucrose on a weight basis. The purified Brazzein(A28D) was found to be 1660 times sweeter than sucrose on a weight basis.

TABLE 6

Sensory Analysis of Purified Brazzzein

| Molecule | Experimental Threshold % [g/100 mL] | Relative Sweetness (by weight) |
| --- | --- | --- |
| Sucrose | 1 | 1 |
| Brazzein(A28D) | 0.0006 | 1660 |

(ix) SDS-PAGE Analysis

Protein expression was analyzed by SDS-PAGE on 15% Tris-Glycine gels. To analyze protein in the cell culture medium, 17 μL of cell free supernatant (corresponding to 0.07% of total culture volume) was mixed with 17 μL of 2× reducing sample buffer, heated for 5 mins in a PCR machine, briefly spun and loaded into the gel. The gel was run at a constant voltage of 125V till the dye front exited the gel. The gels were washed in Milli-Q water for 1 hour and stained with Coomassie Stain. To analyze protein in whole cells, frozen cell pellets were thawed, re-suspended in 50 μL of Milli-Q water. 17 μL of resuspended cells were mixed with 17 μL of 2× Reducing Sample Buffer, heated for 5 mins in a PCR machine, briefly spun and loaded into the gel. The gel was run at constant voltage of 125V till the dye front exited it. The gels were washed in Milli-Q water for 1 hour and stained with Coomassie Stain.

(x) Thermal Stability and Protein Estimation

Cell free supernatant from (i) was heated to 90° C. for 1 hour in a water bath and spun at 17,500 g for 30 mins. The supernatant was analyzed by SDS-PAGE. Protein quantitation was done using BCA assay kit. As a result of heating, most of the endogenous E. coli proteins present in the cell free supernatant precipitated, leaving >90% pure Brazzein in solution. Protein estimation of the supernatant from the heated and spun sample demonstrated a yield of 0.56 g/L of Brazzein (FIG. 11).

(xi) N-Terminal Sequencing

Protein was separated on SDS-PAGE and transferred onto a 0.22 urn pore size PVDF membrane. The membrane was stained with Coommassie Blue till protein bands appeared. The membrane was transferred to Milli-Q water. The band corresponding to Brazzein was cut out with a clean scalpel and submitted for N-terminal sequencing of the first five amino acids. Results from the N-terminal sequencing matched the expected sequence of Type III Brazzein.

---

What is claimed is:

1. A process of secreting a Brazzein peptide into a nutrient broth, the process comprising:
   culturing an *E. coli* cell comprising a recombinant nucleic acid in the nutrient broth comprising dextrose to generate an *E. coli* culture, wherein the recombinant nucleic acid comprises:
   (i) a nucleic acid sequence encoding the Brazzein peptide,
   (ii) a nucleic acid sequence encoding a signal leader amino acid sequence,
      wherein the signal leader amino acid sequence is fused at a 5' end of the Brazzein peptide, and
      wherein the signal leader amino acid sequence is operable to direct extracellular secretion of the Brazzein peptide, and
   (iii) an expression control sequence operable to direct expression of the nucleic acid sequence encoding the signal leader amino acid sequence and the nucleic acid sequence encoding the Brazzein peptide; and
   activating the expression control sequence to generate an extracellularly secreted Brazzein peptide, the activating comprising adding an inducing agent to the nutrient broth and wherein:
   (a) the expression control sequence is lactose inducible,
   (b) the inducing agent is selected from the group consisting of: Lactose, isopropylthiogalactoside (IPTG) and a Lactose analogue,
   (c) activating the expression control sequence directs expression of the nucleic sequence encoding the signal leader amino acid sequence and the nucleic acid sequence encoding the Brazzein peptide, and
   (d) the signal leader amino acid sequence directs the extracellular secretion of the Brazzein peptide into the nutrient broth.

2. The process according to claim 1, further comprising: periodically measuring an optical density (OD 600) of the *E. coli* culture, and adding the inducing agent to the nutrient broth when the *E. coli* culture has an optical density (OD 600) of 0.4.

3. The process according to claim 1, wherein the Brazzein peptide has an amino acid sequence selected from the group consisting of: amino acids 23-75 of SEQ ID NO: 8 and amino acids 23-75 of SEQ ID NO: 2.

4. The process according to claim 1, wherein the signal leader sequence is selected from the group consisting of pelB, ompA, Bla, PhoS, MalE, LivK, LivJ, MglB, AraF, AmpC, RbsB, MerP, CpdB, Lpp, LamB, OmpC, PhoE, OmpF, TolC, BtuB, and LutA.

5. The process according to claim 4, wherein the signal leader sequence is pelB.

6. The process according to claim 1, wherein the nutrient broth comprises 0.1% (w/v) dextrose.

7. The process according to claim 1, wherein the nutrient broth is TB.

8. The process according to claim 1, wherein the nutrient broth is TB, wherein the nutrient broth comprises 0.1% (w/v) dextrose, and wherein the inducing agent is Lactose.

9. The process according to claim 8, wherein the inducing agent is at a concentration of 5 mM.

10. A process for isolating a Brazzein peptide from a nutrient broth comprising dextrose, the process comprising:
    culturing an *E. coli* cell comprising a recombinant nucleic acid in the nutrient broth to generate an *E. coli* culture, wherein the recombinant nucleic acid comprises:
    (i) a nucleic acid sequence encoding a Brazzein peptide,
    (ii) a nucleic acid sequence encoding a signal leader amino acid sequence fused to a 5' end of the nucleic acid sequence encoding the Brazzein peptide,
    wherein cellular translation generates the Brazzein peptide having the signal leader amino acid sequence located at a 5' end,
    wherein the signal leader amino acid sequence is operable to direct extracellular secretion of the Brazzein peptide, and
    (iii) an expression control sequence operable to direct expression of the nucleic acid sequence encoding the signal leader amino acid sequence and the nucleic acid sequence encoding the Brazzein peptide;
    activating the expression control sequence to generate an extracellulary secreted Brazzein peptide, the activating comprising adding an inducing agent to the nutrient broth, and wherein:
    (a) the expression control sequence is lactose inducible,
    (b) the inducing agent is selected from the group consisting of:
    Lactose, isopropylthiogalactoside (IPTG) and a Lactose analogue,
    (c) activating the expression control sequence directs expression of the nucleic sequence encoding the signal leader amino acid sequence and the nucleic acid sequence encoding the Brazzein peptide, and
    (d) the signal leader amino acid sequence directs the extracellular secretion of the Brazzein peptide into the nutrient broth; and
    separating the *E. coli* culture to form a cell pellet and a supernatant, wherein the supernatant comprises the Brazzein peptide.

11. The process according to claim 10, further comprising purifying the supernatant to yield a purified Brazzein peptide.

12. The process according to claim 10, wherein the Brazzein peptide has an amino acid sequence selected from the group consisting of: amino acids 23-75 of SEQ ID NO: 8 and amino acids 23-75 of SEQ ID NO: 2.

13. The process according to claim 10, wherein the nutrient broth comprises 0.1% (w/v) dextrose).

14. The process according to claim 10, wherein the nutrient broth is TB.

15. The process according to claim 10, wherein the nutrient broth is TB, wherein the nutrient broth comprises 0.1% (w/v) dextrose, and wherein the inducing agent is Lactose.

16. The process according to claim 15, wherein the inducing agent is at a concentration of 5 mM.

17. The process according to claim 10, further comprising: periodically measuring an optical density (OD 600) of the *E. coli* culture, and adding the inducing agent to the nutrient broth when the *E. coli* culture has an optical density (OD 600) of 0.4.

18. The process according to claim 10, wherein the signal leader sequence is selected from the group consisting of pelB, ompA, Bla, PhoS, MalE, LivK, LivJ, MglB, AraF, AmpC, RbsB, MerP, CpdB, Lpp, LamB, OmpC, PhoE, OmpF, TolC, BtuB, and LutA.

19. The process according to claim 18, wherein the signal leader sequence is pelB.

* * * * *

SEQUENCE LISTING

```
<160> NUMBER OF SEQ ID NOS: 11

<210> SEQ ID NO 1
<211> LENGTH: 234
<212> TYPE: DNA
<213> ORGANISM: Artificial sequence
<220> FEATURE:
<223> OTHER INFORMATION: Synthetic:  Nucleotide sequence encoding pel B
      and Brazzein

<400> SEQUENCE: 1
atgaaatacc tgctgccgac cgctgctgct ggtctgctgc tcctcgctgc ccagccggcg      60
atggccgaca atgtaaaaa ggtgtatgaa aactatccgg tctcaaaatg tcaactggcg     120
aaccaatgta actacgactg taaactggcg aaacatgcgc gtagcggtga atgcttctac     180
gatgaaaaac gcaatctgca atgtatctgt gactactgtg aatattaata atga          234

<210> SEQ ID NO 2
<211> LENGTH: 75
<212> TYPE: PRT
<213> ORGANISM: Artificial Sequence
<220> FEATURE:
<223> OTHER INFORMATION: Synthetic:  Amino acid sequence of pel B
      conjugated to Brazzein

<400> SEQUENCE: 2

Met Lys Tyr Leu Leu Pro Thr Ala Ala Ala Gly Leu Leu Leu Leu Ala
1               5                   10                  15

Ala Gln Pro Ala Met Ala Asp Lys Cys Lys Lys Val Tyr Glu Asn Tyr
            20                  25                  30

Pro Val Ser Lys Cys Gln Leu Ala Asn Gln Cys Asn Tyr Asp Cys Lys
        35                  40                  45

Leu Ala Lys His Ala Arg Ser Gly Glu Cys Phe Tyr Asp Glu Lys Arg
    50                  55                  60

Asn Leu Gln Cys Ile Cys Asp Tyr Cys Glu Tyr
65                  70                  75

<210> SEQ ID NO 3
<211> LENGTH: 38
<212> TYPE: DNA
<213> ORGANISM: Artificial sequence
<220> FEATURE:
<223> OTHER INFORMATION: Synthetic:  PelBLun-FNcoNde - primer

<400> SEQUENCE: 3
gcgcgcccat ggcatatgaa atacctgctg ccgaccgc                              38

<210> SEQ ID NO 4
<211> LENGTH: 51
<212> TYPE: DNA
<213> ORGANISM: Artificial sequence
<220> FEATURE:
<223> OTHER INFORMATION: Synthetic:  Braz-Rbam-primer
```

<400> SEQUENCE: 4
gcgcgcggat cctcattatt aatattcaca gtagtcacag atacattgca g    51

<210> SEQ ID NO 5
<211> LENGTH: 52
<212> TYPE: DNA
<213> ORGANISM: Artificial sequence
<220> FEATURE:
<223> OTHER INFORMATION: Synthetic:  BRAZ-A28DRSOE-primer

<400> SEQUENCE: 5
caccgctacg cgcatgttta tccagtttac agtcgtagtt acattggttc gc    52

<210> SEQ ID NO 6
<211> LENGTH: 22
<212> TYPE: DNA
<213> ORGANISM: Artificial sequence
<220> FEATURE:
<223> OTHER INFORMATION: Synthetic:  BRAZ-A28DFSOE - primer

<400> SEQUENCE: 6
gataaacatg cgcgtagcgg tg    22

<210> SEQ ID NO 7
<211> LENGTH: 234
<212> TYPE: DNA
<213> ORGANISM: Artificial sequence
<220> FEATURE:
<223> OTHER INFORMATION: Synthetic:  nucleotide Sequence encoding pelB
      conjugated to Brazzein(A28D)

<400> SEQUENCE: 7
atgaaatacc tgctgccgac cgctgctgct ggtctgctgc tcctcgctgc ccagccggcg    60
atggccgaca atgtaaaaa ggtgtatgaa actatccgg tctcaaaatg tcaactggcg    120
aaccaatgta actacgactg taaactggat aaacatgcgc gtagcggtga atgcttctac    180
gatgaaaaac gcaatctgca atgtatctgt gactactgta atattaata atga    234

<210> SEQ ID NO 8
<211> LENGTH: 75
<212> TYPE: PRT
<213> ORGANISM: Artificial Sequence
<220> FEATURE:
<223> OTHER INFORMATION: Synthetic:  Amino Acid Sequence of
      pelB-Brazzein(A28D)

<400> SEQUENCE: 8

Met Lys Tyr Leu Leu Pro Thr Ala Ala Ala Gly Leu Leu Leu Leu Ala
1               5                   10                  15

Ala Gln Pro Ala Met Ala Asp Lys Cys Lys Lys Val Tyr Glu Asn Tyr
            20                  25                  30

Pro Val Ser Lys Cys Gln Leu Ala Asn Gln Cys Asn Tyr Asp Cys Lys
        35                  40                  45

Leu Asp Lys His Ala Arg Ser Gly Glu Cys Phe Tyr Asp Glu Lys Arg
    50                  55                  60

Asn Leu Gln Cys Ile Cys Asp Tyr Cys Glu Tyr
65                  70                  75

<210> SEQ ID NO 9
<211> LENGTH: 93
<212> TYPE: DNA
<213> ORGANISM: Artificial sequence

```
<220> FEATURE:
<223> OTHER INFORMATION: Synthetic:  ompANde - primer

<400> SEQUENCE: 9
gcgcgcccat ggcaatgaaa aaaacggcaa ttgcgatagc ggttgcgcta gctggttttg         60
ccacggtggc gcaggctgac aaatgtaaaa agg                                     93

<210> SEQ ID NO 10
<211> LENGTH: 231
<212> TYPE: DNA
<213> ORGANISM: Artificial sequence
<220> FEATURE:
<223> OTHER INFORMATION: Synthetic:  nucleotide Sequence encoding ompA
      conjugated to Brazzein(A28D)

<400> SEQUENCE: 10
atgaaaaaaa cggcaattgc gatagcggtt gcgctagctg ttttgccac ggtggcgcag         60 gctgacaaat gtaaaaggt gtatgaaaac tatccggtct caaaatgtca actggcgaac        120
caatgtaact acgactgtaa actggataaa catgcgcgta gcggtgaatg cttctacgat        180
gaaaaacgca atctgcaatg tatctgtgac tactgtgaat attaataatg a                231

<210> SEQ ID NO 11
<211> LENGTH: 74
<212> TYPE: PRT
<213> ORGANISM: Artificial Sequence
<220> FEATURE:
<223> OTHER INFORMATION: Synthetic:  Amino Acid Sequence of
      ompA-Brazzein(A28D)

<400> SEQUENCE: 11

Met Lys Lys Thr Ala Ile Ala Ile Ala Val Ala Leu Ala Gly Phe Ala
1               5                   10                  15

Thr Val Ala Gln Ala Asp Lys Cys Lys Lys Val Tyr Glu Asn Tyr Pro
            20                  25                  30

Val Ser Lys Cys Gln Leu Ala Asn Gln Cys Asn Tyr Asp Cys Lys Leu
        35                  40                  45

Asp Lys His Ala Arg Ser Gly Glu Cys Phe Tyr Asp Glu Lys Arg Asn
    50                  55                  60

Leu Gln Cys Ile Cys Asp Tyr Cys Glu Tyr
65                  70
```